(12) United States Patent
Symes

(10) Patent No.: US 10,016,719 B2
(45) Date of Patent: Jul. 10, 2018

(54) REDUCING FOULING IN AMINE SYSTEMS

(71) Applicant: ExxonMobil Chemical Patents Inc., Baytown, TX (US)

(72) Inventor: Richard A. Symes, Midlothian (GB)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/495,182

(22) Filed: Apr. 24, 2017

(65) Prior Publication Data

US 2017/0341015 A1 Nov. 30, 2017

Related U.S. Application Data

(60) Provisional application No. 62/341,712, filed on May 26, 2016.

(51) Int. Cl.
| | |
|---|---|
| *B01D 53/14* | (2006.01) |
| *B01D 1/06* | (2006.01) |
| *B01D 5/00* | (2006.01) |
| *B01D 19/00* | (2006.01) |
| *C07C 7/11* | (2006.01) |

(52) U.S. Cl.
CPC .......... *B01D 53/1425* (2013.01); *B01D 1/06* (2013.01); *B01D 5/006* (2013.01); *B01D 19/0073* (2013.01); *B01D 53/1462* (2013.01); *B01D 53/1493* (2013.01); *C07C 7/11* (2013.01); *B01D 2252/204* (2013.01)

(58) Field of Classification Search
None
See application file for complete search history.

(56) References Cited

U.S. PATENT DOCUMENTS

| | | | |
|---|---|---|---|
| 3,696,162 A | 10/1972 | Kniel | |
| 3,926,591 A | 12/1975 | Wildmoser et al. | |
| 4,857,283 A | 8/1989 | Madden, II | |
| 6,334,886 B1 | 1/2002 | Barnes, Jr. et al. | |
| 6,989,046 B1 | 1/2006 | Slim et al. | |
| 9,701,558 B1 * | 7/2017 | Bader | C02F 9/00 |
| 2004/0118126 A1 | 6/2004 | Ong et al. | |
| 2015/0298026 A1 * | 10/2015 | Radzicki | C10L 3/10 |
| | | | 95/264 |

(Continued)

FOREIGN PATENT DOCUMENTS

| | | |
|---|---|---|
| EP | 0040892 | 12/1981 |
| EP | 0824142 | 2/1998 |

(Continued)

*Primary Examiner* — Tam M Nguyen

(57) ABSTRACT

The invention generally relates to processes for reducing fouling in amine systems and to equipment useful in such processes. Such amine systems are useful for removing one or more acidic gases such as $CO_2$ or $H_2S$ from olefin containing hydrocarbon streams. The invention generally relates to minimizing residence time of foulant and foulant precursors at the relatively high temperature found in the amine regenerator and/or to purging the foulant and foulant precursors from the regenerator system. This is accomplished by operating the regenerator column as a stripper (no reflux) and re-routing reflux liquid containing foulant or foulant precursors to a processing location that is less prone to fouling or, optionally, by replacing the reflux liquid with fresh make-up amine or water.

10 Claims, 1 Drawing Sheet

(56) References Cited

U.S. PATENT DOCUMENTS

2016/0045841 A1* 2/2016 Kaplan ................ B01J 19/0093
429/49

FOREIGN PATENT DOCUMENTS

| EP | 2818220 | 12/2014 |
| WO | 2014/039758 | 3/2014 |
| WO | 2016/090357 | 6/2016 |

* cited by examiner

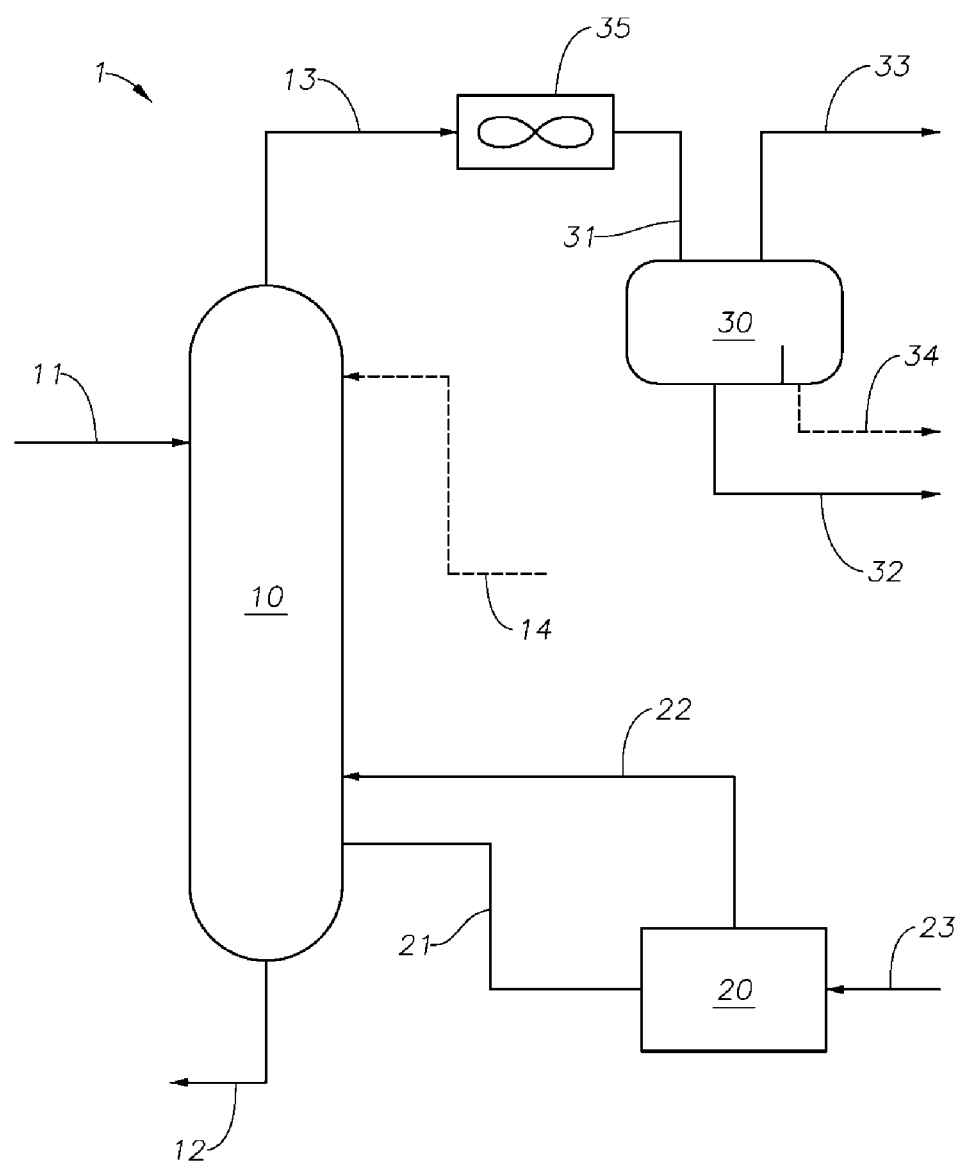

REDUCING FOULING IN AMINE SYSTEMS

PRIORITY CLAIM

The present application claims the benefit of and the priority to U.S. Ser. No. 62/341,712, filed May 26, 2016 and is incorporated by reference in its entirety.

FIELD OF THE INVENTION

The invention generally relates to processes for reducing fouling in amine systems and to equipment useful in such processes. Such amine systems are useful for removing one or more acidic gases such as carbon dioxide ($CO_2$) or hydrogen sulfide ($H_2S$) from olefin containing hydrocarbon streams.

BACKGROUND OF THE INVENTION

Olefins are used to produce many useful products. For example, ethylene and/or propylene are polymerized to produce polymer, such as polyethylene, polypropylene, ethylene-propylene copolymer, etc. Olefins are produced by many conventional processes, including: (1) catalytically converting alcohol, such as methanol; (2) pyrolysing a hydrocarbon-containing feed, as in steam cracking; or (3) catalytically cracking a hydrocarbon feed, as in fluidized catalytic cracking, hydrocracking, etc. Besides olefins, effluents from these processes contain acidic gases for example, $H_2S$ and/or $CO_2$. The effluent also contains diolefin molecules for example, propadiene, cyclopentadiene, isoprene, or butadiene. Additionally, the effluent can contain aldehyde, such as acetaldehyde.

Amine may be utilized for removing one or more acidic gases from a process stream containing olefins. For example, $CO_2$ and $H_2S$ are removed from a steam cracker effluent by contacting the effluent with an amine mixture by an acid gas scrubbing process in an absorber.

Inside the absorber, the amine mixture absorbs acid gases, like $CO_2$ and $H_2S$, and removes them from the olefins process stream. The amine mixture containing the acid gases exits the absorber and is conducted to an amine regeneration system where the mixture is heated in a regenerator to release the acid gases and produce a regenerated amine mixture. Conventional designs of amine regenerators cool the regenerator overhead to produce a reflux liquid that is sent back to the regenerator tower. The regenerated amine mixture exiting the regeneration system, mostly free of acid gases, is returned to the absorber where the process is repeated.

A significant hurdle to operation of an acid gas scrubbing process is buildup of polymerized foulant, particularly in the regeneration equipment. Polymerization fouling causes the acid gas scrubbing process to limit capacity for the broader olefin production process resulting in significant negative financial impact.

One way to lessen polymerization fouling in the amine regeneration system involves contacting the amine with an aromatic stream such as pyrolysis gasoline to remove a majority of foulant precursors upstream of the regenerator. See, e.g., U.S. Pat. No. 3,926,591, incorporated by reference. Foulant precursors are transferred to the aromatic stream, producing a rich aromatic stream (i.e., an aromatic stream rich in foulant) which is conducted away from the process. However, even with this known procedure, it is not possible to keep all the foulant precursors away from the regeneration system. As a consequence, polymerization fouling of regeneration system equipment, particularly equipment in and downstream of the regenerator that is contacted by the foulant-containing regenerated amine, remains a capacity limiting problem for the broader olefin process.

U.S. Pat. No. 6,989,046, incorporated by reference, describes adding a heavy hydrocarbon solvent upstream of the regenerator and leaving a portion of the solvent entrained in the amine being fed to the regenerator. However, the specific gravity of the heavy hydrocarbon solvent limits separation and removal efficiency. Further, adding solvent upstream of the regenerator leads to undesirable solvent in the regenerator overhead stream.

Pending U.S. patent application Ser. No. 14/629,602, incorporated by reference, describes adding aromatic hydrocarbon downstream of the regenerator.

Nevertheless, fouling in amine systems, particularly in or downstream of the regenerator, remains a limitation to operating run-length and capacity.

SUMMARY OF THE INVENTION

The present invention is an improved process that reduces fouling in or downstream of amine regenerator towers. The invention generally relates to minimizing residence time of foulant and foulant precursors at the relatively high temperature found in an amine regenerator and/or to purging the foulant and foulant precursors from the regenerator system. This is accomplished by operating a regenerator column as a stripper (no reflux) and re-routing reflux liquid containing foulant or foulant precursors to a processing location that is less prone to fouling or, optionally, by replacing the reflux liquid with fresh water and/or make-up amine.

The present invention relates to an amine regeneration process, comprising several steps. First, provide a rich amine mixture comprising water, amine, acid gas, foulant, and foulant precursor. Second, heat the rich amine mixture to form a vapor stream and a liquid regenerated amine mixture. The vapor stream comprises at least a portion of the acid gas, water, amine, foulant, and foulant precursor. The liquid regenerated amine mixture comprises the remaining water and amine. Third, cool and separate the vapor stream to form a sour gas stream comprising at least a portion of the acid gas and a sour amine stream comprising water, amine, foulant and foulant precursor. Fourth, conduct the entire sour amine stream away.

The present invention also relates to replacing reflux liquid with fresh water and/or fresh make-up amine mixture. That is, where reflux is desired or required to improve separation efficiency in the regenerator, the reflux should not be the foulant and foulant precursor containing sour amine stream, but rather could be fresh water and/or make-up amine Accordingly, in an aspect of the invention, the vapor stream is contacted with liquid water or with liquid makeup amine mixture to remove at least a portion of the water and amine from the vapor stream before cooling and separating the vapor stream.

One advantage of the present invention is the process may be applied to existing amine regenerator facilities without need for costly retrofit of new regenerator facilities. Another advantage is the invention addresses a root cause of fouling by removing foulant precursors and foulant from the system before they have opportunity for further polymerization in the regenerator and on downstream equipment. Additionally, the present invention has proven suitable for olefin process streams derived from steam cracking heavy hydrocarbons feedstocks including crude oil which tend to generate significant foulant and foulant precursors in the amine system.

These and other features, aspects, and advantages of the present invention will become better understood from the following description, appended claims, and accompanying drawings.

BRIEF DESCRIPTION OF THE DRAWING

The FIGURE schematically illustrates an amine regenerator system.

DETAILED DESCRIPTION OF THE INVENTION

Definitions

For the purposes of this description and its appended claims, the term "foulant precursors" means any one or a combination of 1) products of base-induced condensation reactions involving carbonyl compounds in an amine-containing mixture, 2) reactive diolefin molecules, or 3) heat stable salts that lead to degraded amine byproducts.

For the purposes of this description and its appended claims, the term "foulant" means any one or a combination of 1) polymer products of base-induced condensation reactions involving carbonyl compounds in an amine-containing mixture, whether formed by aldol condensation products, by shearing, a combination thereof, or otherwise, 2) sulfur-based polymers formed from $H_2S$ addition across the double bonds in diolefins, in the aldol condensation chain, or in acetaldehyde, 3) polymer products of diolefin molecules, or 4) degraded amine byproducts.

For the purposes of this description and its appended claims, the term "sour" means containing $H_2S$ and/or mercaptans.

When numerical lower limits and numerical upper limits are listed herein, ranges from any lower limit to any upper limit are contemplated. The term "comprising" is synonymous with the term "including". Likewise whenever a composition, an element or a group of components is preceded with the transitional phrase "comprising", it is understood to also contemplate the same composition or group of components with transitional phrases "consisting essentially of," "consisting of", "selected from the group consisting of," "including," or "is" preceding the recitation of the composition, component, or components, and vice versa.

Description

Many methods for producing unsaturated hydrocarbons produce an effluent process stream containing $C_{2+}$ monoolefins, diolefins, "acid gas" molecules such as one or more of $CO_2$ or $H_2S$, and carbonyls, such as acetaldehyde. Such methods include catalytically converting alcohol, pyrolysing a hydrocarbon-containing feed, as in steam cracking, or catalytically cracking a hydrocarbon feed, as in fluidized catalytic cracking, hydrocracking, etc. Effluent process streams produced from these methods can also contain methane and hydrogen.

At least a portion of the $CO_2$ and/or $H_2S$ acid gas may be removed from process streams containing $C_{2+}$ hydrocarbon by contacting the process stream in an absorber with a mixture comprising one or more amines and water. The $CO_2$ and/or $H_2S$ are absorbed by the amine in the absorber and released when the amine is heated (regenerated) in a regenerator. Before contacting the process stream, the amine mixture is called a "regenerated" amine mixture (also known as a "lean" amine mixture—i.e., containing less $CO_2$ and $H_2S$). Thus, the regenerated amine mixture is located downstream of the regenerator and upstream of the absorber. After contacting the process stream (and absorbing at least a portion of one or more of the process stream's acidic gases) the regenerated amine mixture becomes a "rich" amine mixture. Thus, the rich amine mixture is located downstream of the absorber and upstream of the regenerator. Typically, the regenerated amine mixture comprises at least 10% (preferably at least 50%, even more preferably at least 75%) less $CO_2$ and/or $H_2S$ acid gas (molar basis) than the corresponding rich amine mixture. The $CO_2$ and/or $H_2S$ acid gas concentration (also known as acid gas "loading") can range from at least 0.01 (preferably at least 0.05) moles of acid gas per mole of amine in the regenerated amine mixture up to 0.75 (preferably up to 0.5) moles of acid gas per mole of amine in the rich amine mixture.

Because amine-containing mixtures are bases (albeit relatively weak bases, with a pH generally in the range of from about 10 to about 12), base-induced condensation reactions can occur (e.g., aldol condensation reactions) involving the carbonyl compounds, including aldehydes (e.g., acetaldehyde) and/or ketones. Foulant precursors and foulant resulting from condensation can appear as an oil having a reddish, reddish-brown, or black color ("red oil"). Red oil can be present in an aromatics-soluble liquid phase, or, more commonly, in the form of an emulsion of the red oil and an aqueous component. The emulsion can comprise the amine mixture, aldol condensation products, and polymer formed from the aldol condensation products. Shearing of the red oil, e.g., shearing of the emulsion, has been observed to result in further polymerization of the aldol condensation products.

Additionally, it is believed that diolefins are carried into the amine mixture by solubility in the amine mixture and also by at least the mechanism where the amine mixture condenses some heavier diolefin hydrocarbons that are present in the hydrocarbon process stream, e.g., cyclopentadiene, isoprene, or butadiene. The reactive diolefins undergo addition type polymerization to various degrees promoted by the heat of the regenerator and shearing of circulation pumps, even to the point of reaching a molecular weight which renders certain polymer species insoluble in the amine mixture such that they precipitate out of solution. Foulant can also form from degraded amine byproducts, for example, hydroxyethyl-ethylenediamine (HEED), that form from heat stable salts. Sulfur-based foulant can result from $H_2S$ addition across double bonds in diolefins, in the aldol condensation chain, or in the addition product of acetaldehyde.

Foulant precursors and foulant in the regenerated amine mixture adhere to equipment contacted by the mixture including the interconnecting piping, for example, the regenerator tower, reboiler, and a feed-effluent heat exchanger downstream of the regenerator and upstream of the absorber. This polymer buildup reduces heat transfer and/or pump capacity and consequently removal efficiency of $CO_2$ and $H_2S$ from the process stream. Removing the deposited polymer, generally with the regenerator (and absorber) off-line, is time consuming and expensive.

Buildup of foulant in or downstream of the regenerator can be reduced by minimizing exposure of foulant and foulant precursors to the heat present in the amine regenerator and/or by purging the foulant and foulant precursors from the regenerator system. This is accomplished by operating the regenerator column as a stripper (i.e. without reflux) and re-routing any reflux liquid containing foulant or foulant precursors to a processing location that is less prone to fouling. Alternatively, if reflux is desired to improve separation efficiency, the foulant and foulant precursor containing reflux liquid can be carried away and replaced with fresh make-up amine mixture and/or water.

The rich amine mixtures will now be described in further detail. The rich amine mixture comprises one or more amines, and optionally water. Conventional amine mixtures are suitable for use in the invention, but the invention is not limited thereto. If desired, the rich amine mixture can further comprise one or more physical solvents, e.g., those disclosed in U.S. Pat. No. 3,989,811 and/or one or more additives (e.g., for lessening the effects of fouling) such as those disclosed in U.S. Pat. No. 6,372,121. The amines utilized can be, e.g., alkanolamines and mixtures thereof. Alkanolamines are molecules containing both amine and hydroxyl groups. The rich amine mixtures may comprise 5.0 wt. % to 70.0 wt. % of one or more primary, secondary, or tertiary alkanolamine, based on the weight of the first feed. The amine can include of one or more of monoethanolamine, diethanolamine, methyl diethanolamine, or dipropanolamine, and the amine mixture's amine can comprises ≥10.0 wt. % of one or more of monoethanolamine ("MEA"), diethanolamine ("DEA"), methyl diethanolamine ("MDEA"), or dipropanolamine ("DPA"), based on the weight of amine in the rich amine mixture. Preferably, the rich amine mixture may comprise an aqueous mixture of one or more amine and water.

The invention will now be described in more detail with respect to a broader amine system for removing acid gas from a process stream containing $C_{2+}$ olefin, foulant precursors, and acid gas molecules such as one or more of $CO_2$ and $H_2S$. The invention is not limited to this embodiment, and this description is not meant to foreclose other embodiments within the broader scope of the invention.

An amine regenerator system 1 is illustrated by the FIGURE. A rich amine mixture comprising water, amine, acid gas, foulant, and foulant precursor is provided via conduit 11 to regenerator 10. The rich amine mixture is conducted via conduit 21 to reboiler 20 where heating medium, e.g., steam, supplied to reboiler 20 by conduit 23 heats the rich amine mixture indirectly. The heated rich amine mixture is returned to regenerator 10 via conduit 22. A vapor stream comprising the volatile acid gas, at least a portion of amine, as well as foulant and foulant precursors separates from the heated rich amine mixture and exits overhead of regenerator 10 via conduit 13. A regenerated amine mixture comprising the remaining liquid amine exits the regenerator via conduit 12. The vapor stream 13 is cooled in condenser 35 and conducted via conduit 31 to overhead separation drum 30. A sour amine stream formed as condensate from the cooled vapor stream and comprising water, amine, at least a portion of the vapor stream's foulant and foulant precursors is entirely conducted away via conduit 32. A sour gas stream comprising at least a portion of the acid gas from the vapor stream is removed via conduit 33. The sour amine stream 32 and sour gas stream 33 are labeled "sour" to indicate presence of $H_2S$ and/or mercaptans in these streams. Optionally, a liquid hydrocarbon stream comprising at least a portion of the vapor stream's foulant and foulant precursors is skimmed and conducted away via conduit 34. Also optional, liquid make-up amine or make-up water may be added via conduit 14 to regenerator 10 and used as reflux to improve separation of amine and water from acid gas.

The sour amine stream 32 may be conducted to another processing unit where the foulant and foulant precursors can be better handled. In one embodiment, the sour amine stream 32 is conducted to a steam cracking process primary fractionator (not shown).

With respect to a broader amine system, regenerated amine mixture 12 is provided to an amine absorber (not shown). A process stream (not shown) comprising acid gas such as $H_2S$ and/or $CO_2$ is provided the amine absorber where the process stream contacts and combines with the regenerated amine mixture. At least a portion of the process stream's $H_2S$ and/or $CO_2$ acid gases are removed from the process stream. An upgraded process stream (not shown) is conducted away from the absorber. The upgraded process stream contains lesser amounts of $H_2S$ and/or $CO_2$ than the process stream, such as 50% less $H_2S$ and/or $CO_2$, or 75% less, or 90% less (on a molar basis). The remaining portion of the process stream's $H_2S$ and/or $CO_2$ acidic gases are transferred from the process stream to the regenerated amine mixture in the absorber, and the $H_2S$ and/or $CO_2$ acid gases (or ionized components thereof) are conducted away from the absorber as components of the rich amine mixture via conduit 11. Additionally, at least a portion of the process stream's foulant precursors are transferred to and conducted away as components of the rich amine mixture.

Operating conditions in the absorber (not shown) are well known to one having ordinary skill in the art and are determined in part by the type of amine as well as the types and amounts of acid gases present in the process stream. A non-limiting example of the absorber operating conditions includes a temperature in the range of about 35° C. to about 55° C., a pressure in the range of about 5 bar to about 20 bar, and a sufficient amine mixture flow rate to maintain the concentration of acid gas in the rich amine below 0.75 moles of acid gas per mole of amine Although not required in all cases, the invention is compatible with additional acid gas removal stages (not shown in the FIGURE), such as those utilizing caustic for removing $CO_2$ from the upgraded process stream.

The rich amine mixture is conducted via line 11 to regenerator 10 for regeneration. Optionally, the rich amine mixture is pre-heated in a feed-effluent heat exchanger (not shown) prior to being introduced to the regenerator 10. Regeneration conditions in regenerator 10 are well known to one having ordinary skill in the art and may include a temperature in the range of about 105° C. to about 150° C. The regeneration is conducted under conditions that are sufficient to remove from the rich amine mixture at least a portion (at least 10%, preferably at least 50%, more preferably at least 75% on a molar basis) of the rich amine mixture's $H_2S$ and/or $CO_2$ ions. $H_2S$ and/or $CO_2$ removed from the rich amine mixture is conducted away from regenerator 10 via line 13. The $H_2S$ can be, for example, converted to elemental sulfur in a conventional process, such as the Claus process. The regenerated amine mixture is conducted away from regenerator 10 via line 12.

In an optional preliminary step (not illustrated in the FIGURE), the rich amine mixture in line 11 is contacted with an aromatic mixture (not shown) upstream of the regenerator to remove at least a portion of the foulant precursors and produce an upgraded rich amine mixture (comprising fewer foulant precursors) and a rich aromatic mixture (comprising more foulant precursors). Suitable examples of such an optional preliminary step are disclosed in U.S. Pat. Nos. 3,598,881, and 3,926,591; and U.S. patent application Ser. No. 61/814,602 which are incorporated herein in their entirety. Subsequent to the optional preliminary step, the upgraded rich amine is conducted via line 11 to regenerator 10 as specified to produce the regenerated amine mixture. However, it has been observed that this optional preliminary step does not keep all the foulant precursors away from the regeneration system as described later in this application. Suitable aromatics mixtures comprise aromatics, such as ≥50.0 wt. % (preferably ≥75 wt. %, more preferably ≥90 wt. %) of aromatics, based on the weight of the aromatics mixtures. The aromatics can be a mixture of one or more of $C_{7+}$ aromatics (for example, $C_{8+}$ aromatics, $C_{9+}$ aromatics, preferably $C_{10+}$ aromatics). The aromatics mixtures generally comprises ≥90.0 wt. % hydrocarbon, based on the weight of the aromatics mixtures. Suitable aromatics mixtures in this optional preliminary step have a specific gravity <0.950, for example, ≤0.945, ≤0.940, preferably ≤0.935, such as ≤0.930, ≤0.925, or ≤0.920 to assist with separation of the aromatic mixture. The specific gravity of the aromatics mixtures may be ≥0.800, for example, ≥0.805, ≥0.810, or ≥0.820.

Optionally, the foulant precursors and foulant originate from a process stream produced by steam cracking hydrocarbon feedstock. In another option, the process stream is produced by steam cracking heavy hydrocarbon feedstock, such as crude oil. In another option, the process stream comprises ≥0.15 wt. % $H_2S$, based on the weight of the process stream. In yet another option, the process stream comprises ≥0.10 wt. % $CO_2$, based on the weight of the process stream. In still yet another option, the process stream comprises ≥0.15 wt. % $H_2S$ and ≥0.10 wt. % $CO_2$, based on the weight of the process stream.

Although the steam cracking feedstock's hydrocarbon can comprise one or more of light hydrocarbons such as methane, ethane, propane, butane etc., it can be particularly advantageous to utilize the invention in connection with a pyrolysis feedstock comprising a significant amount of higher molecular weight hydrocarbons because the pyrolysis of these molecules generally results in more acid gas and/or more foulant precursors than does the pyrolysis of lower molecular weight hydrocarbons. As an example, the pyrolysis feedstock can comprise ≥1.0 wt. % or ≥25.0 wt. % based on the weight of the pyrolysis feedstock of hydrocarbons that are in the liquid phase at ambient temperature and atmospheric pressure.

In certain aspects, the steam cracking feedstock's hydrocarbon comprises ≥5 wt. % of non-volatile components, based on the weight of the hydrocarbon portion, e.g., ≥30 wt. %, such as ≥40 wt. %, or in the range of 5 wt. % to 50 wt. %. Non-volatile components are the fraction of the hydrocarbon feed with a nominal boiling point above 1100° F. (590° C.) as measured by ASTM D-6352-98, D-7580. These ASTM methods can be extrapolated, e.g., when a hydrocarbon has a final boiling point that is greater than that specified in the standard. The hydrocarbon's non-volatile components can include coke precursors, which are moderately heavy and/or reactive molecules, such as multi-ring aromatic compounds, which can condense from the vapor phase and then form coke under the operating conditions encountered in the present process of the invention. Examples of suitable hydrocarbons include, one or more of steam cracked gas oil and residues, gas oils, heating oil, jet fuel, diesel, kerosene, gasoline, coker naphtha, steam cracked naphtha, catalytically cracked naphtha, hydrocrackate, reformate, raffinate reformate, Fischer-Tropsch liquids, Fischer-Tropsch gases, natural gasoline, distillate, virgin naphtha, crude oil, atmospheric pipestill side streams and bottoms, vacuum pipestill streams including bottoms, wide boiling range naphtha to gas oil condensates, heavy non-virgin hydrocarbon streams from refineries, vacuum gas oils, heavy gas oil, naphtha contaminated with crude, atmospheric residue, heavy residue, C4/residue admixture, naphtha/residue admixture, gas oil/residue admixture, and crude oil. The steam cracking feedstock's hydrocarbon can have a nominal final boiling point of at least about 600° F. (315° C.), generally greater than about 950° F. (510° C.), typically greater than about 1100° F. (590° C.), for example greater than about 1400° F. (760° C.). Nominal final boiling point means the temperature at which 99.5 weight percent of a particular sample has reached its boiling point.

EXAMPLES

The examples describe amine systems for removing acid gas from a process stream containing $C_{2+}$ olefin, foulant precursors, and $CO_2$ and $H_2S$ acid gas where the process stream is produced by steam cracking. The invention is not limited to embodiment where the process stream is produced by steam cracking, and this description is not meant to foreclose other embodiments within the broader scope of the invention.

Example 1 (Comparative)

A rich amine mixture is provided to a regenerator. The rich amine mixture comprises foulant and foulant precursors derived from a process stream produced by steam cracking where the process stream comprises $H_2S$ and $CO_2$. The rich amine mixture is an upgraded rich amine mixture as described previously in which a portion of the foulant and foulant precursors have been removed by contacting with an aromatic mixture. Nevertheless, the rich amine mixture contains foulant and foulant precursors. The rich amine mixture is heated in the regenerator and produces a vapor stream comprising at least a portion of the rich amine mixture's acid gas, i.e. the $H_2S$ and $CO_2$, as well as a portion of the foulant and foulant precursors. The vapor stream is cooled and the liquid portion is returned to the regenerator as reflux. Polymer formation is observed in the regenerator and downstream equipment contacted by the regenerated amine The operating capacity of the amine system and the steam cracking process were limited by the fouling.

Example 2

A rich amine mixture is provided to a regenerator. The rich amine mixture comprises foulant and foulant precursors derived from a process stream produced by steam cracking where the process stream comprises $H_2S$ and $CO_2$. The rich amine mixture is heated in the regenerator and produces a vapor stream comprising at least a portion of the rich amine mixture's acid gas, i.e., the $H_2S$ and $CO_2$, as well as a portion of the foulant and foulant precursors. The vapor stream is cooled and the liquid portion conducted away to the steam cracking unit's primary fractionator. No liquid reflux is returned to the regenerator. The regenerator operates without limiting capacity between regular scheduled steam cracking process maintenance shutdowns (i.e., the regenerator and amine system operate without limiting olefin production between turnarounds).

Example 3

A rich amine mixture is provided to a regenerator. The rich amine mixture comprises foulant and foulant precursors derived from a process stream produced by steam cracking where the process stream comprises $H_2S$ and $CO_2$. The rich amine mixture is heated in the regenerator and produces a vapor stream comprising at least a portion of the rich amine mixture's acid gas, i.e., the $H_2S$ and $CO_2$, as well as a portion of the foulant and foulant precursors. The vapor stream is cooled and the liquid portion conducted away to the steam cracking unit's primary fractionator. Clean water make-up is provided to the regenerator as liquid reflux. The regenerator operates without limiting capacity between regular scheduled steam cracking process maintenance shutdowns (i.e., the regenerator and amine system operate without limiting olefin production between turnarounds).

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains.

What is claimed is:

1. An amine regeneration process, comprising:
   (a) providing a rich amine mixture comprising water, amine, acid gas, foulant, and foulant precursor;
   (b) heating the rich amine mixture to form a vapor stream and a liquid regenerated amine mixture, the vapor stream comprising at least a portion of the acid gas, water, amine, foulant, and foulant precursor, the liquid regenerated amine mixture comprising the remaining water and amine;
   (c) cooling and separating the vapor stream to form a sour gas stream comprising at least a portion of the acid gas and a sour amine stream comprising water, amine, foulant and foulant precursor, and residual acid gas, wherein the separation includes stripping without reflux; and
   (d) conducting the entire sour amine stream away to a location that is less prone to fouling than the amine regeneration process.

2. The process of claim 1, further comprising contacting the vapor stream with liquid water or with liquid makeup amine mixture comprising water and amine to remove at least a portion of the water and amine from the vapor stream before the cooling and separating of the vapor stream in step (c).

3. The process of claim 1 further comprising, conducting the sour amine stream for further processing in a steam cracking process primary fractionator.

4. The process of claim 1, wherein the rich amine mixture is derived from an upgraded rich amine mixture.

5. The process of claim 1, wherein the heating of the rich amine mixture occurs in a regenerator tower.

6. The process of claim 1, wherein the vapor stream is cooled in an overhead condenser.

7. The process of claim 1, wherein the rich amine mixture's amine content comprises 5.0 wt. % to 60.0 wt. % of one or more primary, secondary, or tertiary alkanolamines.

8. The process of claim 1, wherein the foulant precursors and foulant originate from a process stream produced by i) catalytically converting alcohol, ii) pyrolysing a hydrocarbon-containing feed, including steam cracking, or iii) catalytically cracking a hydrocarbon feed, including fluidized catalytic cracking and hydrocracking.

9. The process of claim 1, wherein the foulant precursors and foulant originate from a process stream produced by steam cracking.

10. The process of claim 1, wherein the foulant precursors and foulant originate from a process stream produced by steam cracking crude oil.

\* \* \* \* \*